United States Patent [19]

Messing et al.

[11] 4,149,936

[45] Apr. 17, 1979

[54] HIGH SURFACE LOW VOLUME FUNGAL BIOMASS COMPOSITE

[75] Inventors: Ralph A. Messing, Horseheads; Robert A. Oppermann, Painted Post, both of N.Y.

[73] Assignee: Corning Glass Works, Corning, N.Y.

[21] Appl. No.: 918,928

[22] Filed: Jun. 26, 1978

Related U.S. Application Data

[63] Continuation-in-part of Ser. No. 833,275, Sep. 14, 1977, abandoned.

[51] Int. Cl.$^2$ .............................................. C12B 1/00
[52] U.S. Cl. ...................... 195/56; 195/53; 195/54; 195/116; 195/DIG. 11
[58] Field of Search ........... 195/116, 63, 68, DIG. 11, 195/52, 53, 54, 57, 59, 60, 28 R, 115

[56] References Cited

U.S. PATENT DOCUMENTS

| | | | |
|---|---|---|---|
| 3,616,246 | 10/1971 | Cherry | 195/81 |
| 3,850,751 | 11/1974 | Messing | 195/63 |
| 3,875,008 | 4/1975 | Yoshino et al. | 195/63 |
| 3,892,580 | 7/1975 | Messing | 106/41 |
| 3,983,000 | 2/1976 | Messing et al. | 195/63 |
| 4,001,085 | 1/1977 | Keyes | 195/68 |
| 4,071,409 | 1/1978 | Messing et al. | 195/63 |

FOREIGN PATENT DOCUMENTS 979547 12/1975 Canada ................................... 195/116

OTHER PUBLICATIONS

Methods in Enzymology, vol. 44, pp. 148–159 (1976).

*Primary Examiner*—Lionel M. Shapiro
*Attorney, Agent, or Firm*—William E. Maycock; Clinton S. Janes, Jr.

[57] ABSTRACT

Immobilized microbe composite comprising a porous, high surface area inorganic support having a controlled population of fungus-like microbes bonded to the internal surfaces of the pores, the support being water insoluble, non-toxic to the microbes, and having a controlled porosity such that at least 70% of the pores, on a pore size distribution basis, have a pore diameter at least as large as the smallest diameter of the fungal spore but less than about sixteen times the largest spore diameter. The composites are especially useful in situations requiring a high biomass surface within a relatively small volume.

19 Claims, 3 Drawing Figures

HIGH SURFACE LOW VOLUME FUNGAL BIOMASS COMPOSITE

RELATED APPLICATIONS

Patent Application Ser. No. 833,278, filed Sept. 14, 1977, in the names of R. A. Messing and R. A. Oppermann, and entitled "High Surface Low Volume Biomass Composite." The present application is a continuation-in-part of application Ser. No. 833,275, filed Sept. 14, 1977, now abandoned.

BACKGROUND OF THE INVENTION

1. Field

This disclosure is concerned generally with the attachment and growth of microbes on inorganic surfaces. Specifically, the disclosure is concerned with providing a porous inorganic support for the immobilization of a controlled population of fungus-like organisms which reproduce via spores and exhibit mycelial growth, collectively referred to herein as fungi or fungus-like microbes.

2. Prior Art

The preparation and use of composites consisting of microbes (bacteria, yeast cells, etc.) fixed on the surfaces of support materials is very old and well known. Typically, a film or slime of microbes is allowed to grow over the surfaces of the support. The resultant film provides a biomass which, depending on the microbes involved, can be used in various practical applications. For example, one of the earlier trickling filter fermentation systems involved using wood shavings or other supports as a packing material which was placed in a container such as a barrel. A liquid raw material was allowed to trickle through the packing and, in some cases, air was allowed to pass upward through the packing. As the liquid was circulated with a simple pump, a film of microbes would form on the surfaces of the packing, thereby resulting in a relatively large accumulation of useful biomass which, depending on the type of microbial film (anaerobic or aerobic conditions), could be used to ferment sugars to alcohol (anaerobic) or convert alcohol to acids (aerobic). The latter process could be used to make vinegar. Early trickling filter systems of that type were commonly referred to as Schuetzenbach generators.

Numerous variations of that type of fermenting system are well known. See, for example, U.S. Pat. No. 454,586 to Bachmann which describes a fermenting vat for the fermentation of sugar solutions to a variety of products. The system consists of a flow-through vat containing a porous packing material. In that patent it was pointed out that the fermentation "germs" of a liquid substrate appeared to multiply more rapidly within the pores and on the surfaces of the packing than when the "germs" were freely floating in the liquid.

Other microbe support systems describing the use of high surface area microbe supports are shown in U.S. Pat. No. 2,440,545 (saw dust, alfalfa chops, cut straw, glass beads, stone grit, etc.); U.S. Pat. No. 3,709,364 (use of sand particles for sewage treatment); U.S. Pat. No. 3,402,103 (series of baffles in a flow through reactor upon which bacterial films are formed); and Indian Pat. No. 43542 (use of porous particles of pumice as supports for yeast cells). From a sampling of the prior art, it is quite clear that others have long appreciated certain advantages of using porous, high surface area inorganic materials as supports for microbial films.

While it can be readily appreciated that there exists a relationship between the porosity of a given support material and the useable surface area that the material provides in a given application, we have now found, quite surprisingly, that in the case of porous supports for fungi and fungus-like microbes, there exists a range of pore sizes which, vis-a-vis the microbe size, provides an extremely large surface but low volume for a high biomass concentration. Details of our findings and the immobilized microbe composites resulting therefrom are described in detail herein.

SUMMARY OF THE INVENTION

Our immobilized microbe composites comprise a porous, high surface area inorganic support material having a controlled population of fungi or fungus-like microbes bonded to the internal surfaces of the pores, the support being water-insoluble, non-toxic to the microbes, and having a controlled porosity such that at least 70% of the pores, on a pore size distribution basis, have a pore diameter at least as large as the smallest dimension of the fungal spore but less than about sixteen times the largest dimension of the fungal spore. Such composites provide a relatively large biomass surface within a relatively small volume. In preferred embodiments, the population of microbes comprises a single species of fungus and the inorganic support comprises material in which pore size distribution can be readily and economically controlled (e.g. amorphous or glass materials such as fritted glasses, or crystalline materials such as spinel-zirconia, cordierite-like materials, etc.). Examples of products that are produced by the fungus-like organisms of this disclosure (spore formers demonstrating mycelial growth) include antibiotics (e.g. penicillin, streptomycin), citric acid, and enzymes (e.g. glucose isomerase).

SPECIFIC EMBODIMENTS

Figure 1:
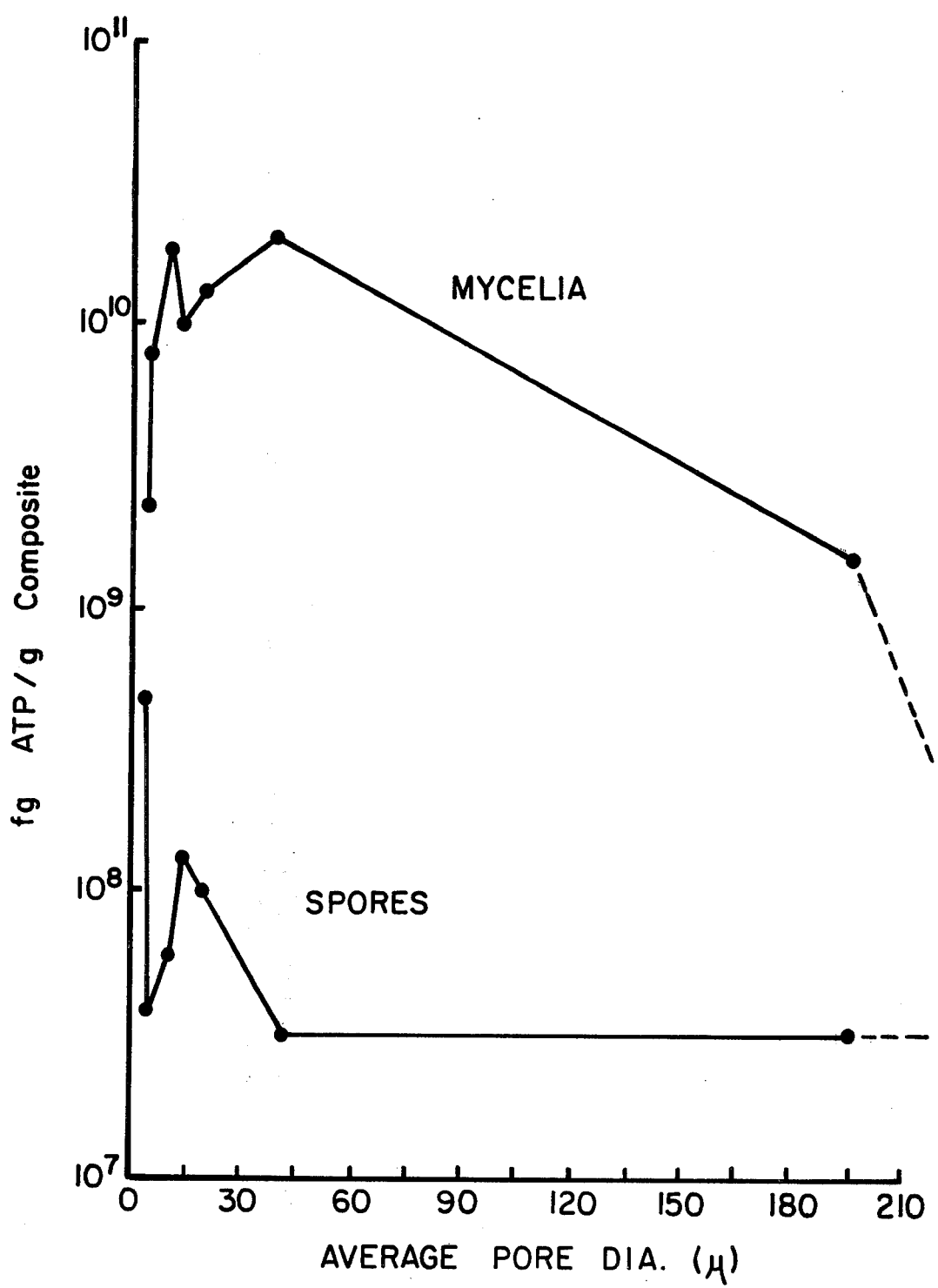
FIG. 1 is a graph illustrating relationships existing between the average pore diameter of several inorganic supports and the number of *Aspergillus niger* bonded thereto for both immobilized spores alone and fungal mycelia.

The importance of accumulating very large biomass surfaces in a limited reaction volume can be appreciated by considering some of the practical applications of immobilized microbes in general. It is well known, for example, that the mere multiplication of microbial cells can be a basis for the rapid generation of proteinaceous matter. By providing optimum conditions favoring microbial cell reproduction on a continuous basis, the accumulated cells can, under some conditions, be processed for their protein value. This is the basis for so-called single cell protein technology (SCP).

Although SCP production is presently available on a continuous (cf. batch) basis using systems known as chemostats or turbidostats, it can be appreciated that, except for wall effects, the bulk of the reproducing cells are merely suspended in a nutrient medium. Although there are certain advantages in those systems, the flow rates (or SCP production rates) are limited by that rate above which there begins to occur a washout of the microbial seed material. Very simply stated, washout refers to a situation where, because of high flow rates of nutrients through a continuous system, the loss of microbes within the reactor is greater than the gain due to cell reproduction.

Both chemostats and turbidostats are subject to washout, thus placing an upper limit on microbe production rates. Since immobilized microbes having a high amount of biomass surface per unit volume would not be as subject to high-flow rate washout as chemostat-type systems, the value of such an immobilized system becomes readily apparent, provided cellular requirements such as nutrients, waste removal, pH, oxygen supply, etc., can be satisfied.

The value of having a high biomass surface area per unit volume is also apparent in that area of fermentation concerned with the production of secondary metabolites. For example, since secondary metabolites are generally produced in the stationary phase of microbial life cycle processes, and since the total amount of secondary metabolites produced thereby will depend on the amount of biomass surface available to release the metabolites on a continuous basis, it is clear that any system which provides a means for providing and prolonging the stationary phase of a high biomass surface will provide an ideal secondary metabolite production system. As in the case of SCP production, the retention of a large biomass surface in a given volume through which nutrients can flow at high rates also permits the rapid removal of metabolic waste products as well as useful products. Our system can also be used for primary metabolite production.

Yet another area in which the technology of this disclosure has application is the field of analytical microbiology where there are clear advantages in having available immobilized fungi composites capable of uniform delivery of a stable fungi population. The composites of this disclosure can thus be used as fungal standards which provide a reliable and convenient method of storing and handling large quantities of microbes per unit volume.

Our present disclosure is grounded on our observation that there exists a unique physical relationship between a given population of fungi which reproduce by spore formation and exhibit mycelial growth and a porous support material upon which the microbes form a film such that it is possible to achieve a maximum amount of biomass surface with a minimum amount of immobilized microbe volume. To a very limited extent this observation is somewhat similar to that associated with immobilized enzyme technology wherein it has been shown that there exists a relationship between the amount of active enzyme that can be loaded on a given weight (or volume) of porous support material. See for example, U.S. Pat. No. 3,850,751, which discloses an optimum support pore size range of about 100Å to 1000Å for most immobilized enzyme systems. This disclosure is also similar in principle to the disclosures in our pending application, cited above, wherein we have shown unique relationships exist between the pore sizes of supports and microbes which reproduce by fission (e.g. bacteria).

It should be understood that our findings are applicable only to immobilized microbe composites in which the microbes reproduce by spore formation and exhibit mycelial growth and our composites exclude those microbes which reproduce by other means (fission, budding, etc.). Hence, as used herein, the expressions microbe(s), fungi, or fungus-like organism refer to those microbes (primarily fungi and algae) which reproduce by spore formation and demonstrate mycelial growth.

It should also be understood that for reasons discussed herein, the support or carrier material should be inorganic rather than organic.

An inorganic carrier material has a variety of marked advantages. The first is that microbes do not readily attack inorganic materials since their nutrient requirements are primarily focused to carbon and nitrogen containing materials. Organic carriers such as carbohydrates, proteins, etc. are readily attacked not only by the microbes but also by the extracellular enzymes that are elaborated by the organism. As the organic carrier is destroyed, the accumulation of microbes is reduced. In addition to durability, the inorganic carrier has the advantage of dimensional stability when contrasted to most organic carriers. By retaining the pore morphology under a variety of pressure and flow conditions, the microbe is protected from deformation and subsequent lysing. Again, this is an advantage in terms of biomass accumulation.

An additional advantage of an inorganic carrier is its relatively high density. Most organic materials have densities in the neighborhood of 1.0 or less while most of the inorganic materials have densities greater than 2.0. Under these circumstances, an inorganic material having an equal porosity with an organic material on a mass basis would occupy a lesser volume; therefore, on a volume basis the inorganic material could concentrate a greater biomass. The higher density inorganic materials have additional advantages in that lower pressure drops are experienced in plug-flow reactors and will perform better in a fluidized bed reactor, since the particles will not flow to and remain at the surface, but, rather, they will continuously be agitated within the body of the solution.

A further advantage associated with the use of inorganics as fungi supports, especially according to the present disclosure, is that controlled porosity of the support can be obtained relatively simply and economically using commonly available starting materials.

Although there exists considerable information about how fungal films are formed over the surfaces of supports, less information appears to exist about the effective mechanism by which the fungi actually attach to the support. It is well known, however, that most microbes will attach to and reproduce on all but the most toxic substances. As used herein, the expression "bonded," when applied to the mode of attachment of the microbes or microbe film to the support, includes all modes of attachment whether by physical or chemical bonds or both. As a matter of convenience in the examples below, microbes were simply allowed to bond to the support by what appeared to be adsorptive forces. However, residues of polyisocyanates or silane coupling agents can be used to coat the surfaces of the support, thereby providing a possible basis for chemical bonding of the cells to the support via the coatings. The cells may also be crosslinked in place over or on the support surfaces.

The controlled population of microbes includes fungi or algae cells of a given species, all being in the same general size range, as well as other collections of microbes having a similarity of sizes such that at least 70% of the pores of the support have pore diameters large enough to readily admit substantially all members of the population and, for purposes of maintaining maximum usable surface area and protection against microbial washout, less than about sixteen times the maximum dimension of the largest spore.

The smallest and largest major dimensions of most fungus-like organisms can be found in textbooks or can be determined using known techniques. Whether at least 70% of the pores of a given inorganic support have pore diameters equal to one to 16 times the smallest to largest given major microbe dimensions can be determined by known means such as via the mercury intrusion porosimetry distribution technique. All such supports should have a high surface area. As used herein, the expression high surface area refers to a support having a surface area greater than about 0.01 $m^2$/gram.

Our observation that there exists an optimum pore size distribution for inorganic supports of a given population of fungi can be appreciated best by interpreting our experimental results vis-a-vis theoretical physical considerations. Since most spores are almost spherical, essentially there is only one dimension to be considered and that is the diameter of the sphere. As the spore germinates, long fibers (mycelium) develop. It is the mycelium (vegetative bodies) that is responsible for the production of secondary metabolites and additional spore formations. In order to allow for the growth of the mycelium which is considerably larger in the major dimension than the spore, a pore diameter substantially greater than that simply utilized to accumulate the spore is required if multiple branching occurs. The upper pore size limit is demonstrated in the examples below.

While it can be appreciated that the pore diameter of the support should be at least as large as the smallest spore to readily admit the microbe, a higher loading of microbes or a more effective utilization of the largely internal surface area occurs when the pores are somewhat larger than the minimum size needed to readily admit the spores. We have found, as shown below, that the upper limit of pore size which in general permits the most effective utilization of surface area per unit volume of support is about sixteen times the largest spore dimension of the microbe bonded therein.

It should be noted that in some cases where microbe reproduction per se is not of prime concern (e.g., secondary metabolite production where a relatively constant stationary phase is desired), a more effective utilization of internal surface area results when the bulk of the pores is closer in size to the smallest dimension of the spores. Thus, depending on the purpose for which the microbes are to be immobilized, it can be appreciated that, in general, the most efficient use of surface area for bonding a given population of microbes results when a majority (at least 70%) of the pores of a porous inorganic support has pore diameters ranging in sizes equal to the smallest spore dimension to about sixteen times the largest spore dimension. As shown in the examples below, it was found that the peak value for biomass surface accumulation was found when the support pore size was within that range. Specifically, optimal loading results were obtained when at least 70% of the pores had pore diameters about 2-13 times the smallest major microbe dimension.

The importance of controlling pore size distribution of the porous inorganic support is shown by comparing the biomass loading results obtained with separate porous supports, only one of which had a tightly controlled pore size distribution. In general, the experimental results appeared to indicate that at least about 70% of the pores should have pore diameters at least as large as the smallest spore size of the fungus studied but less than about sixteen times the largest spore dimension.

In the examples below, the porous supports having a known and reasonably controlled porosity included various fritted glass materials and spinel-zirconia and cordierite-like crystalline materials. The best fritted glass and crystalline supports had at least 70% of their pore sizes within the required range (e.g. 75–100% for the fritted glass, 100% for the spinel-zirconia crystalline materials, and 71–100% for the cordierite-type crystalline materials). The pore size ranges in microns and the average pore size for the exemplary support materials are reported in Tables I, III, and IV, infra.

Because our fungus loading (biomass) determinations involved measuring the number of microbes bonded within the pores of the various porous supports, we could not use conventional plate counting techniques. Instead, the microbe counts were determined using a DuPont Biometer Model No. 760 which determines microbe count based on the amount of ATP present in a given sample. The actual procedure used was as follows: To approximately 10–20 mg of composite add 0.5 ml of 90% DMSO (Dimethylsulfoxide) in water. Mix the suspension vigorously for 10 seconds. Allow the suspension to stand 20 minutes, then add 4.0 ml of pH 7.4 0.01M MOPS (Morpholinopropane sulfonic acid) buffer. Mix vigorously and store in ice until it is to be read in the biometer. 10 $\mu$l of this solution is added to a cuvette already in the biometer which contains the luciferin-luciferase mixture. The extracted ATP reacts with the enzyme mixture to produce light which is determined quantitatively and is proportional to the amount of ATP.

The reliability of the results using the above technique is ±20%. Further information concerning the use and reliability of the Biometer measuring technique can be found in the following publication: Instruction Manual, 760 Luminescence Biometer, E. I. DuPont De Nemours & Co., Instrument Products Division, Wilmington, Del. 19898, December 1970.

Our findings and specific methods of making the composites of the present invention are illustrated in the examples below. The representative microbe bonded to the various supports by the indicated techniques was the fungus *Aspergillus niger*. Unless otherwise indicated, the support materials were in particulate form having a particle size in the range of 18–25 mesh, U.S. Standard Sieve.

EXAMPLE I

*Aspergillus niger* (spore diameters observed ranged from 3 through 5 microns). Spores of *A. niger* were eluted from a mature growth in a Blake bottle with a sterile phosphate buffer. The suspension was made to 100 ml with buffer. Ten ml of this spore suspension was added to 50 ml microfernbach flasks which had been dry autoclaved with 1 g of carrier and dried overnight prior to use. After 3 hours of shaking at room temperature the excess spores were poured off, the carrier was washed three times with phosphate buffer, and stored overnight at 8° C. The quantity of spores that was adsorbed by the various carriers was determined by ATP measurement with the DuPont biometer. The results are recorded in the table.

TABLE I

| Average Pore Size (μ) | Pore Distribution (μ) | Carrier Composition | % of Pores in Optimum Range | ATP fg* per g of Carrier |
|---|---|---|---|---|
| 3.5 | 1.5–4 | Fritted Glass | 75 | $4.8 \times 10^8$ |
| 4.5 | 3–6 | Fritted Glass | 100 | $3.8 \times 10^7$ |
| 10 | 2–19 | Cordierite | 93 | $6.0 \times 10^7$ |
| 13 | 8–20 | Fritted Glass | 100 | $1.3 \times 10^8$ |
| 19 | 17–35 | Spinel-Zirconia | 100 | $9.7 \times 10^7$ |
| 40 | 18–100 | Fritted Glass | 91 | $3.1 \times 10^7$ |
| 195 | 170–220 | Fritted Glass | 0 | $3.1 \times 10^7$ |
| Non-porous | — | Borosilicate glass | 0 | $3.4 \times 10^7$ |

*fg - Femtograms ($10^{-15}$ g) with Biometer set for the standard ATP solution at $2.44 \times 10^8$ By observation the average single spore of *A. niger* is 4 microns with spores distributed in the range of 3–5 microns.

In order to determine the optimum pore diameter range for mycelial growth, 0.5 g of each carrier with the immobilized spores was placed in 75 ml of Sabouraud Dextrose broth on a shaker at room temperature. At the end of 27 hours a sample of each carrier was taken and the amount of ATP was determined as a measure of mycelial growth. The results are recorded below in Table II.

TABLE II

*A. niger* Mycelial Growths in Various Carriers

| Average Pore Size (μ) | Pore Distribution (μ) | Carrier Composition | % of Pores in Optimum Range | ATP fg per g of Carrier |
|---|---|---|---|---|
| 3.5 | 1.5–4 | Fritted Glass | 75 | $2.6 \times 10^9$ |
| 4.5 | 3–6 | Fritted Glass | 100 | $7.5 \times 10^9$ |
| 10 | 2–19 | Cordierite | 93 | $1.9 \times 10^{10}$ |
| 13 | 8–20 | Fritted Glass | 100 | $9.3 \times 10^9$ |
| 19 | 17–35 | Spinel-Zirconia | 100 | $1.3 \times 10^{10}$ |
| 40 | 18–100 | Fritted Glass | 91 | $2.0 \times 10^{10}$ |
| 195 | 170–220 | Fritted Glass | 0 | $1.5 \times 10^9$ |
| non-porous | — | Borosilicate glass | 0 | $2.1 \times 10^8$ |

The results recorded in the two tables are plotted in FIG. 1. It should be noted that, although the highest quantity of spores was immobilized in the smallest pore (3.5 microns), the spore was not large enough to allow a great deal of mycelial growth. It should also be noted that the highest recorded value for mycelial growth was in a material that had an average pore diameter of 40 microns, with 91% of the pores being in the range of 1×the smallest spore diameter (3 microns) and 16 times the largest spore diameter (5 microns). Although the spore immobilization curve indicates that approximately the same number of spores was immobilized in the 40 micron material as was immobilized on the non-porous glass, a marked increase in mycelial growth was noted between the 40 micron glass and either the 195 micron or the non-porous glass.

Since an uninterrupted plot between the 40 micron and the 195 micron glass in the growth curve indicates that an 80 micron average pore would allow growth equivalent to that noted at 13 micron, it appears clear that the upper limit of pore size is 80 microns which is 16 times the largest spore diameter (5 microns).

The two following examples are additional evidence of the inventive method for accumulating a fungal type biomass on controlled-pore inorganic carriers. Two different microbes were utilized having two different pore sizes, viz., *Streptomyces olivochromogenes* having spores of about 1–2.5 microns in diameter and *Penicillium chrysogenum* having spores ranging between about 2.5–4.5 microns in diameter.

The spores of both microbes can be immobilized by adsorption on porous inorganic carriers and the quantity of spores immobilized determined via protein analysis. Following the adsorption of the spores, mycelial growth was induced to take place within the pores of the carrier and this growth again measured via protein analysis after growth periods of 24 and 48 hours. Nine carriers were employed in the study having three decidedly disparate compositions.

EXAMPLE II

*Streptomyces olivochromogenes*

Equal amounts of spores in phosphate buffer were added to 0.5 g of each of the carriers. The spores and carriers were allowed to react together for 48 hours. The non-reacted spores were decanted off and the carrier then was washed three times with 2 ml aliquots of sterile phosphate buffer. These non-reacted spores plus the washings were collected, their volume determined and then analyzed for protein content. The quantity of protein adsorbed in the carrier was calculated as the difference between the initial content of protein in the reacting volume containing the spores and that contained in the non-reacted spores plus the washings.

The washed carrier containing the spores was separately transferred to a flask containing 50 ml of Emerson broth medium. Mycelium formation within the carrier pores was evaluated after incubation, with shaking, for 24 hours and 48 hours at room temperature.

At the end of the stated periods of incubation, the carrier was separated from the medium via centrifugation and washed three times with 10 ml of phosphate buffer, pH 7.0. The total quantity of carrier was extracted with 3 ml of phosphate buffer by grinding therewith. Subsequently, 3 ml of 1N NaOH were added thereto, the temperature of the mixture raised to 60° C., and that temperature maintained for one hour for the purpose of hydrolyzing the mycelium. This procedure results in the quantitative release of protein from the mycelium.

To further extract protein, 3 ml of ethyl alcohol were added and the resulting admixture held at room temperature for 0.5 hour. After centrifugation the mixtures were decanted and the quantity of protein determined utilizing Folin reagent, as described by Hill, E. C., Davies, I, Pritchard, J. A., and Byron, D., "Estimation of Microrganisms in Petroleum Products," *Journal of the Institute of Petroleum*, 53, pp. 275, 524 (1967) and by Hauschka, P. V., "Quantitative Determination of α-carboxyglutamic Acid in Proteins," *Analytical Biochemistry*, 80, p. 212 (1977). The measures of the quantities of spores adsorbed by the various carriers and the growth of mycelia therein are recorded in Table III.

TABLE III

Spore Adsorption and Mycelial Growth of *S. olivochromogenes*

| Carrier Pore Ranges (μ) | Average Pore Size (μ) | Carrier Composition | % Pores in Optimum Range | Spore Adsorption (γ Protein)* per g Carrier | Mycelial Growth (γ Protein) per g Carrier | |
|---|---|---|---|---|---|---|
| | | | | | 24 hours | 48 hours |
| 1.5–6 | 3 | Cordierite | 100 | 7 | 86 | $12.8 \times 10$ |
| 1.5–4.5 | 3.5 | Fritted Glass | 100 | 4 | 456 | $13 \times 10^3$ |
| 2–13 | 10 | Cordierite | 100 | 11 | 44 | $14.3 \times 10^3$ |
| 8–20 | 13 | Fritted Glass | 100 | 7 | 246 | $14.6 \times 10^3$ |
| 3–100 | 18 | Cordierite | 71 | 10 | 10 | $14 \times 10^3$ |
| 17–35 | 19 | Spinel-Zirconia | 100 | 13 | 260 | $13.4 \times 10^3$ |
| 18–100 | 40 | Fritted Glass | 53 | 6 | 48 | $11.3 \times 10^3$ |
| 170–220 | 195 | Fritted Glass | 0 | 7 | 52 | — |
| Non-porous | | Borosilicate | 0 | 0 | 0 | 0 |

*The amount of protein exposed to each carrier was 25γ per gram.

Figure 2:
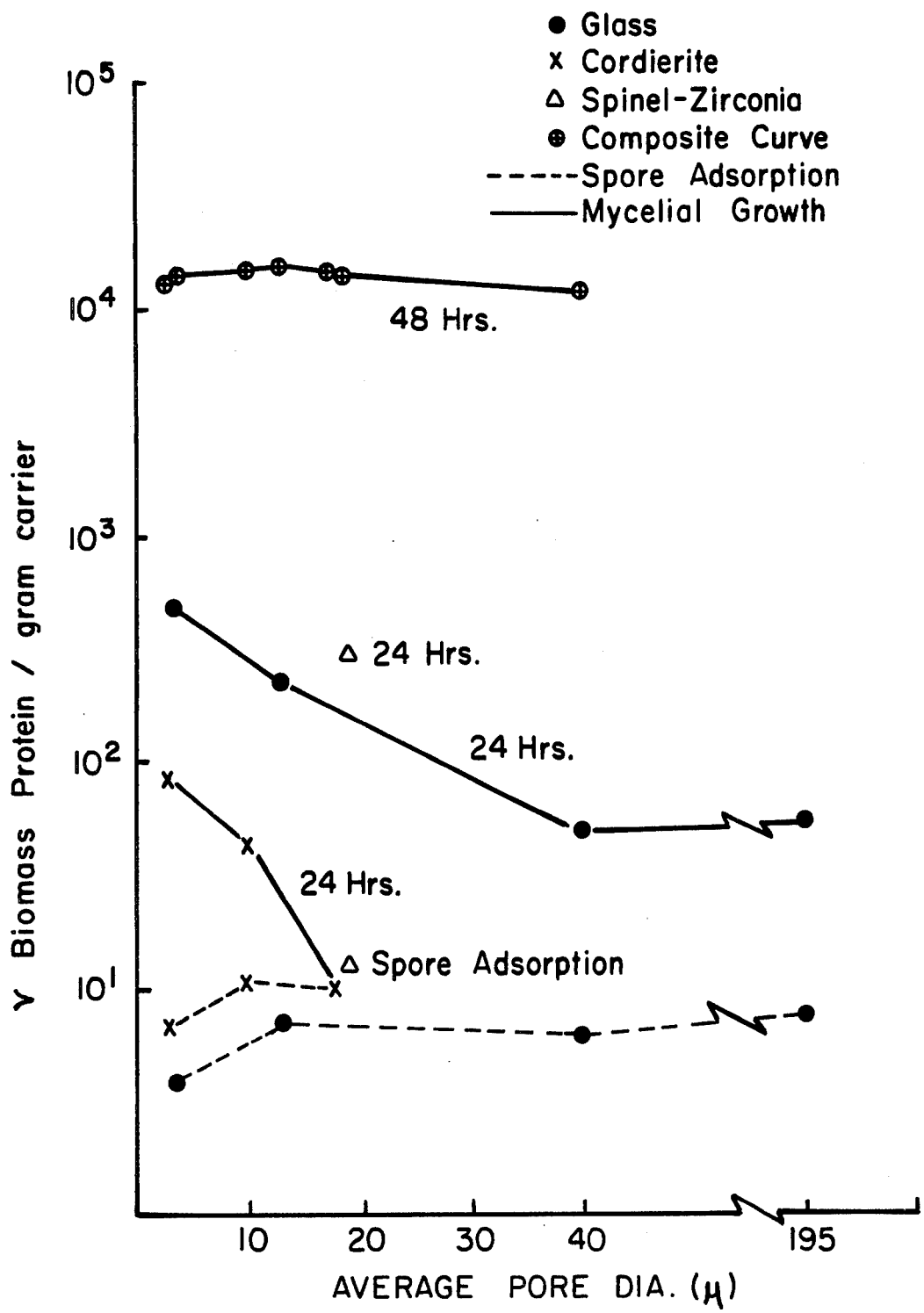
FIG. 2 is a graph depicting relationships existing between the average pore diameter of several inorganic supports and the quantity of *Streptomyces olivochromogenes* adsorbed thereto and the mycelial growth within the pores as determined via protein analysis.

The measurements recorded in Table III are plotted in FIG. 2. It will be observed in the FIGURE that a marked surface effect on spore adsorption and mycelial growth is displayed by the several inorganic carriers. This effect may be unique with *S. olivochromogenes* since it was not noted with *A. niger* above or *P. chrysogenum*, infra. Thus, the more negative fritted glass adsorbs fewer spores but allows much more mycelial growth in the first 24 hour period than the less negative surface of the cordierite-type crystalline material.

Based upon the single exemplary embodiment reported in Table III, it appears that the spinel-zirconia crystalline material accumulates more biomass than either the cordierite or the glass. It should also be noted, however, that this surface effect is not permanent but, rather, is substantially eliminated after a 48 hour growth period. This phenomenon is not totally unexpected and can be explained thusly. The first deposition or monolayer of cells will obviously be affected via direct contact with the carrier surface. Subsequently, as growth continues and this new growth becomes more and more remote from the surface, the dimensions of the carrier pores exert a much greater effect on bioaccumulation than does the surface thereof.

As was noted above, the dimensions of these spores range between about 1–2.5 microns. An examination of the curve representing mycelial growth on fritted glass after 24 hours and the curve representing a composite of mycelial growth on the carriers after 48 hours indicates that a high biomass accumulation occurs at 16 times the largest dimension of the spores, viz., 16×2.5 microns=40 microns. Nevertheless, it must be observed that, in the fritted glass having an average pore size of 40 microns, only 53% of the pores were of a size between 1–40 microns, rather than the at least 70% demanded to yield an operable support. It might also be remarked that, under these circumstances, the accumulation of biomass was not significantly dissimilar from that secured with the fritted glass having an average pore size of 195 microns where none of the pores fall within the 1–40 micron size range.

EXAMPLE III

Pencillium chrysogenum

The technique employed for the immobilization of the spores and the support materials were essentially identical to those described above in Example II. The washing of the carriers and the determination of protein content were conducted in like manner to the description in Example II. The minor and non-substantive differences between the two procedures are two.

First, instead of promoting mycelial growth in Emerson broth, 50 ml of an aqueous medium having a pH of 6.3 with the following composition was utilized for the growth of *P. chrysogenum*: 2% lactose, 1% glucose, 0.2% $KH_2PO_4$, 0.125% $NH_4NO_3$, 0.05% $Na_2SO_4$, 0.025% $MgSO_4$, 0.002% $MnSO_4$, 0.00025% $CuSO_4$, and 0.002% $ZnSO_4$. A single incubation period of 48 hours was employed.

Second, in order to maintain a higher concentration of protein, 2 ml of ethyl alcohol were used for protein extraction rather than 3 ml.

The protein analyses and the measurements of spore contents and mycelial growths were performed in like manner to Example II. These results are recorded in Table IV and are graphically represented in FIG. 3.

TABLE IV

Spore Adsorption and Mycelial Growth of *P. Chrysogenum*

| Carrier Pore Ranges (μ) | Average Pore Size (μ) | Carrier Composition | % Pores in Optimum Range | Spore Adsorption (γ Protein)* per g Carrier | Mycelial Growth (γ Protein) per g Carrier 48 hours |
|---|---|---|---|---|---|
| 1.5–6 | 3 | Cordierite | 71 | 16.66 | 2052 |
| 1.5–4.5 | 3.5 | Fritted Glass | 83 | 16.66 | 168 |
| 2–13 | 10 | Cordierite | 98 | 16.66 | 1563 |
| 8–20 | 13 | Fritted Glass | 100 | 16.66 | 80 |
| 3–100 | 18 | Cordierite | 91 | 16.66 | 1026 |
| 17–35 | 19 | Spinel-Zirconia | 100 | 16.66 | 2640 |
| 18–100 | 40 | Fritted Glass | 85 | 16.66 | 23.2 |
| 170–220 | 195 | Fritted Glass | 0 | 3.22 | 23.2 |
| Non-porous | | Borosilicate | 0 | 4.66 | 0 |

*The amount of protein in the spores exposed to the carrier was 16.66γ of protein per gram of carrier.

Table IV indicates that, contrary to the behavior noted with respect to *S. olivochromogenes* spores, no difference in surface effect is seen when the spores of *P. chrysogenum* are immobilized on the various supports. After mycelial growth for 48 hours, however, the *P. Chrysogenum* appeared to prefer the less negatively charged cordierite over the very negatively charged fritted glass. This, of course, is diametrically opposed to the finding for *S. olivochromogenes*.

Figure 3:
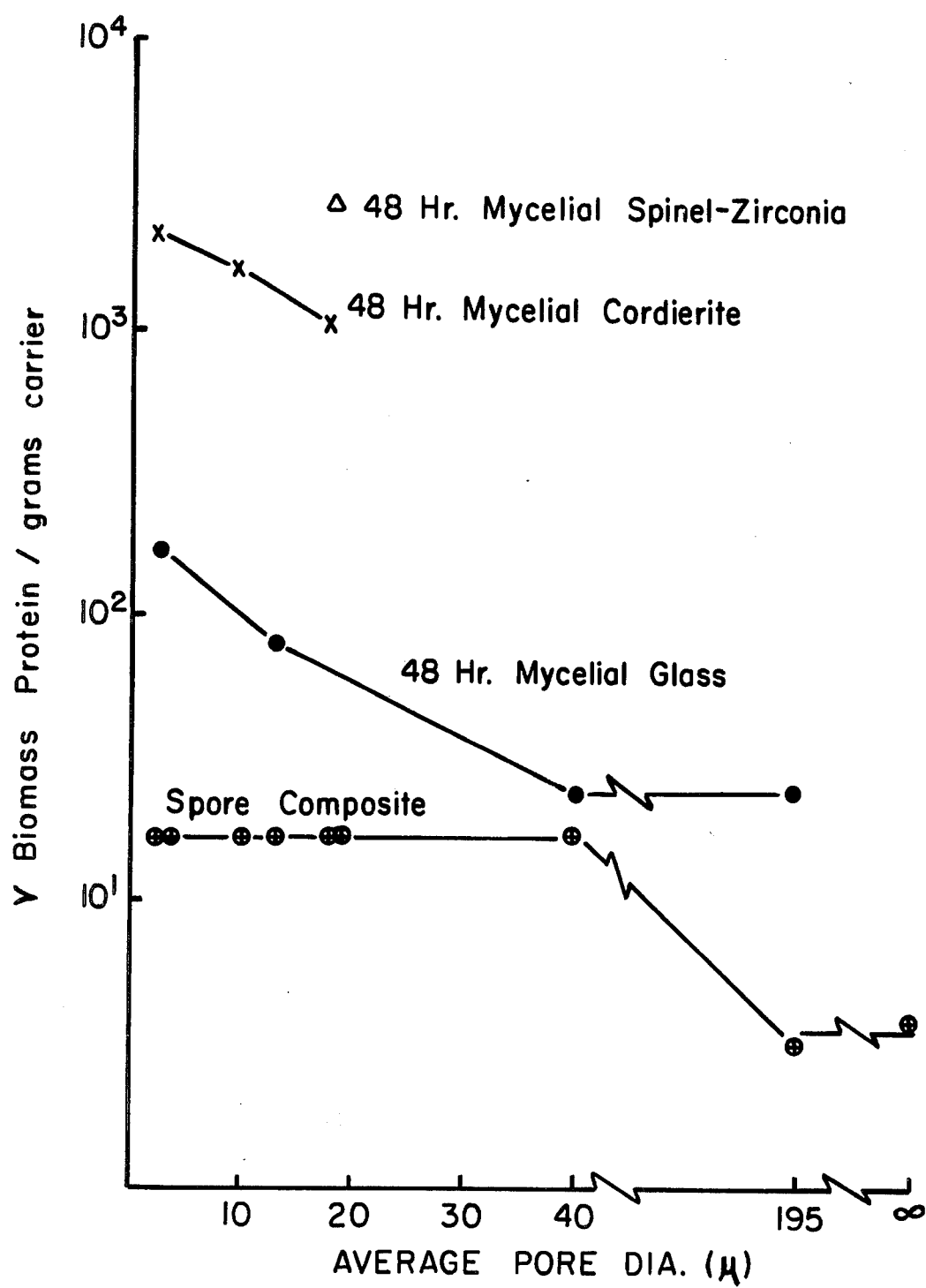
FIG. 3 is a graph setting forth relationships existing between the average pore diameter of several inorganic supports and the quantity of *Penicillium chrysogenum* adsorbed thereto and the mycelial growth within the pores as determined via protein analysis.

Whereas the curve in FIG. 3 of the mycelial growth on the fritted glass support appears to have essentially leveled off at a pore diameter of about 40 microns, only 85% of those pores are within the range of 2.5-72 microns (one times the smallest dimension and 16 times the largest dimension of spores). Nevertheless, justification for including pore diameters of up to 72 microns is evidenced through a study of the spore adsorption and mycelial growth on the cordierite carrier. Hence, as is illustrated in FIG. 3, the curve representing spore adsorption demonstrates a tremendous drop between 40-195 microns and the curve representing mycelial growth after 48 hours seems to parallel the mycelial growth curve for the fritted glass carrier but is markedly higher.

Given this disclosure, it is thought that variations of the above examples will become readily apparent. Hence, it is intended that the invention disclosed herein should be limited only by the following claims.

We claim:

1. An immobilized microbe composite comprising a porous, high surface area inorganic support having a controlled population of fungus-like microbes bonded to the internal surfaces of the pores, the support being water-insoluble, non-toxic to the microbes, and having a controlled porosity such that at least 70% of the pores, on a pore size distribution basis, have a pore diameter at least as large as the smallest spore dimension of the microbes but less than about sixteen times the largest major dimension of the spore.

2. The composite of claim 1 wherein the population of microbes comprises fungi of a single species.

3. The composite of claim 1 wherein the inorganic support comprises an amorphous material.

4. The composite of claim 3 wherein the support comprises fritted glass.

5. The composite of claim 1 wherein the inorganic support comprises a crystalline material.

6. The composite of claim 5 wherein the support comprises a cordierite-like material.

7. The composite of claim 5 wherein the support comprises a spinel-zirconia crystalline material.

8. The composite of claim 1 wherein intermediate the support surfaces and the microbes is a coating material selected from residues of polyisocyanates and silane coupling agents.

9. The composite of claim 1 wherein the microbes comprise spores of a fungus selected from the group of *Aspergillus niger, Streptomyces olivochromogenes*, and *Penicillium chrysogenum*.

10. A method of preparing a high surface area, low volume biomass composite comprising the step of exposing an aqueous spore or mycelial suspension of a controlled population of fungi-like microbes to a sterilized porous inorganic support material having a porosity such that at least 70% of the pores, on a pore size distribution basis, have pore diameters at least as large as the smallest spore dimension of the microbes but less than about sixteen times the largest major dimension of the spore of the microbes, the exposure being under conditions sufficient to result in the bonding of at least some of the microbes onto the internal surfaces defining the pores of the support material.

11. The method of claim 10 wherein, prior to exposure to the microbe suspension, the surfaces of the support are treated with a coating agent selected from polyisocyanates and silane coupling agents.

12. The method of claim 10 wherein the bonding of the microbes onto the internal surfaces defining the pores of the support material is accomplished via adsorption.

13. The method of claim 10 wherein the population of microbes comprises fungi of a single species.

14. The method of claim 10 wherein the support comprises an amorphous material.

15. The method of claim 10 wherein the support comprises fritted glass.

16. The method of claim 10 wherein the support comprises a crystalline material.

17. The method of claim 16 wherein the support comprises a cordierite-like material.

18. The method of claim 16 where the support comprises a spinel-zirconia crystalline material.

19. The method of claim 9 wherein the microbes comprise spores of a fungus selected from the group of *Aspergillus niger, Streptomyces olivochromogenes*, and *Penicillium chrysogenum*.

* * * * *